US008481072B2

(12) United States Patent
Minatelli et al.

(10) Patent No.: US 8,481,072 B2
(45) Date of Patent: *Jul. 9, 2013

(54) COMPOSITION AND METHOD TO ALLEVIATE JOINT PAIN

(75) Inventors: John A. Minatelli, Mt. Dora, FL (US); W. Stephen Hill, Ocala, FL (US); Swati Sebastian Thomas, Chennai (IN); Lingan Rajendran, Chennai (IN); Rudi E. Moerck, Sanford, FL (US)

(73) Assignee: U.S. Nutraceuticals, LLC, Eustis, FL (US)

( * ) Notice: Subject to any disclaimer, the term of this patent is extended or adjusted under 35 U.S.C. 154(b) by 207 days.

This patent is subject to a terminal disclaimer.

(21) Appl. No.: 12/840,372

(22) Filed: Jul. 21, 2010

(65) Prior Publication Data

US 2011/0020316 A1 Jan. 27, 2011

Related U.S. Application Data

(60) Provisional application No. 61/345,652, filed on May 18, 2010, provisional application No. 61/227,872, filed on Jul. 23, 2009.

(51) Int. Cl.
  *A61K 47/00* (2006.01)
(52) U.S. Cl.
  USPC .................................. 424/439; 424/488
(58) Field of Classification Search
  USPC .................... 424/94.63, 439, 488
  See application file for complete search history.

(56) References Cited

U.S. PATENT DOCUMENTS

| 4,801,539 | A  | * | 1/1989 | Akasaka et al. | 435/101 |
|---|---|---|---|---|---|
| 5,527,533 | A  |   | 6/1996 | Tso et al. | 424/422 |
| 6,800,299 | B1 |   | 10/2004 | Beaudoin et al. | 424/522 |
| 7,241,463 | B2 |   | 7/2007 | Nielsen | 426/61 |
| 2004/0180025 | A1 |   | 9/2004 | Long et al. | 424/70.14 |
| 2004/0180851 | A1 |   | 9/2004 | Long et al. | 514/54 |
| 2004/0234587 | A1 |   | 11/2004 | Sampalis | 424/450 |
| 2004/0241249 | A1 |   | 12/2004 | Sampalis | 424/520 |
| 2006/0078625 | A1 |   | 4/2006 | Rockway | 424/538 |
| 2007/0098808 | A1 |   | 5/2007 | Sampalis | 424/523 |
| 2007/0196894 | A1 |   | 8/2007 | Sim et al. | 435/67 |
| 2008/0014282 | A1 |   | 1/2008 | Long et al. | 424/547 |
| 2009/0061067 | A1 |   | 3/2009 | Tilseth et al. | 426/602 |
| 2009/0170808 | A1 |   | 7/2009 | Ling et al. | 514/54 |
| 2009/0181114 | A1 |   | 7/2009 | Minatelli et al. | 424/746 |
| 2009/0181127 | A1 |   | 7/2009 | Minatelli et al. | 426/63 |
| 2009/0258081 | A1 |   | 10/2009 | Minatelli et al. | 424/523 |
| 2010/0143571 | A1 |   | 6/2010 | Breivik | 426/643 |

FOREIGN PATENT DOCUMENTS

| EP | 0601698 B1 | * | 8/1998 |
|---|---|---|---|
| EP | 1724357 | | 11/2006 |
| IN | 201526 | | 2/2007 |
| WO | 03/027267 | | 4/2003 |
| WO | 2004/080388 | | 9/2004 |
| WO | 2004/112776 | | 12/2004 |
| WO | 2011/062953 | | 5/2011 |

OTHER PUBLICATIONS

Gotoh et al. "Effects of the molecular weight of hyaluronic acid and its action mechanisms on experimental joint pain in rats", Annal of the Rheumatic Diseases, 1993, 52:817-822.*
Bergin et al. "Oral hyaluronan gel reduces post operative tarsocrural effusion in the yearling thoroughbred", Equine Veterinary J, 2006, 38(4):375-378.*
Guerin et al. "Haematococcus astaxanthin: applications for human health and nutrition", Trends in Biotechnology, 2003, 21(5):210-216.*
Peer et al. "Tumor-targeted hyaluronan nanoliposomes increase the antitumor activity of liposomal doxorubicin in syngeneic and human xenograft mouse tumor models", Neoplasia, 2004, 6(4):343-353.*
Ruff et al., "*Eggshell Membrane in the Treatment of Pain and Stiffness from Osteoarthritis of the Knee: A Randomized, Multicenter, Double-blind, Placebo-Controlled Clinical Study*," Clinical Rheumatology; Journal of the International League of Associations for Rheumatology; vol. 28, No. 8; Apr. 2009; pp. 907-914.
Ruff et al., "*Eggshell Membrane: A Possible New Natural Therapeutic for Joint and Connective Tissue Disorders. Results from Two Open-Label Human Clinical Studies*," Clinical Interventions in Aging 2009 LNKD-PUBMED: 19554094, vol. 4, May 2009, pp. 235-240.
Ierna et al., "*Supplementation of Diet with Krill Oil Protects Against Experimental Rheumatoid Arthritis*," BMC Musculoskeletal Disorders 2010 LNKD-PUBMED: 20587038, vol. 11, 2010, 11 pages.
Tou et al., "*Krill for Human Consumption: Nutritional Value and Potential Health Benefits*," Nutrition Reviews, vol. 65. No. 2, Feb. 2007, pp. 63-77.
Mendes-Pinto et al., "*Evaluation of Different Cell Disruption Processes on Encrysted Cells of Haematococcus Pluvialis: Effects on Astaxanthin Recovery and Implications for Bio-Availability*," Journal of Applied Phycology, vol. 13, No. 1, Feb. 2001, pp. 19-24.

(Continued)

*Primary Examiner* — Bin Shen
(74) *Attorney, Agent, or Firm* — Allen, Dyer, Doppelt, Milbrath & Gilchrist, P.A.

(57) ABSTRACT

Beneficial and synergistic effects for alleviating joint pain and symptoms of osteoarthritis and/or rheumatoid arthritis have been found with krill oil and/or marine oil in combination with other active constituents, including astaxanthin and polymeric hyaluronic acid or sodium hyaluronate (hyaluronan) in an oral dosage form.

23 Claims, 3 Drawing Sheets

OTHER PUBLICATIONS

Nobre et al., "*Supercritical Carbon Dioxide Extraction of Astaxanthin and Other Carotenoids from the Microalga Haematococcus Pluvialis*," European Food Research and Technology, vol. 223, No. 6, Mar. 2006, pp. 787-790.

Valderrama et al., "*Extraction of Astaxantine and Phycocyanine from Microalgae with Supercritical Carbon Dioxide*," Journal of Chemical and Engineering Data, vol. 48, No. 4, Jul. 2003, pp. 827-830.

Mendes et al., "*Applications of Supercritical CO2 Extraction to Microalgae and Plants*," Journal of Chemical Technology and Biotechnology, vol. 62, No. 1, Jan. 1995, pp. 53-59.

Calder, "*Polyunsaturated Fatty Acids and Inflammation: Therapeutic Potential in Rheumatoid Arthritis*," Current Rheumatology Reviews 2009, vol. 5, No. 4, Nov. 2009, pp. 214-225.

Calder, "*Joint Nutrition Society and Irish Nutrition and Dietetic Institute Symposium on Nutrition and Autoimmune Disease PUFA, Inflammatory Processes and Rheumatoid Arthritis*," Proceedings of the Nutrition Society, vol. 67, No. 4, Nov. 2008, pp. 409-418.

Hurst et al., "*Dietary Fatty Acids and Arthritis*," Prostaglandins, Leukotrienes and Essential Fatty Acids, vol. 82, No. 4-6, Apr. 2010, pp. 315-318.

Sales et al., "*Fish Oil Supplementation in Rheumatoid Arthritis*," Reumatismo, vol. 60, No. 3, Jul. 2008, pp. 174-179.

Kikuchi et al., "*Bibliographical Investigation of Complementary Alternative Medicines for Osteoarthritis and Rheumatoid Arthritis*," Geriatrics and Gerontology International, vol. 9, No. 1, 2009, pp. 29-40.

Balogh et al., "Absorption, Uptake and Tissue Affinity of High-Molecular-Weight Hyaluronan After Oral Administration in Rats and Dogs," Journal of Agricultural and Food Chemistry, published Oct. 30, 2008, pp. 10582-10593.

Deutsch, "*Evaluation of the Effect of Neptune Krill Oil on Chronic Inflammation and Arthritic Symptoms*," Journal of the American College of Nutrition, vol. 26, No. 1, pp. 39-47 (2007).

Bunea et al., "*Evaluation of the Effects of Neptune Krill Oil on the Clinical Course of Hyperlipidemia*," Alternative Medicine Review, vol. 9, No. 4, pp. 420-428 (2004).

Lee et al., "*Astaxanthin Inhibits Nitric Oxide Production and Inflammatory Gene Expression by Suppressing IkB Kinase-Dependent NF-kB Activation*," Molecules and Cells, Jun. 2003, vol. 16, No. 1, pp. 97-105.

Ohgami et al., "*Effects of Astaxanthin on Lipopolysaccharide-Induced Inflammation In Vitro and In Vivo*," Investigative Opthalmology & Visual Science, Jun. 2003, vol. 44, No. 6, pp. 2694-2701.

Mummert et al., "*Synthesis and Surface Expression of Hyaluronan by Dendritic Cells and Its Potential Role in Antigen Presentation*," Journal of Immunology, 2002, pp. 4322-4331.

Termeer et al., "*Hyaluronan—Magic Glue for the Regulation of the Immune Response?*" Trends in Immunology, vol. 24, No. 3, Mar. 2003, pp. 112-114.

McKee et al., "*Hyaluronan Fragments Induced Nitric-Oxide Synthase in Murine Macrophages Through a Nuclear Factor kB-Dependent Mechanism*," Journal of Biological Chemistry, vol. 272, No. 12, Mar. 21, 1997, pp. 8013-8018.

Brown et al., "*Turnover of Hyaluronan in Synovial Joints: Elimination of Labelled Hyaluronan from the Knee Joint of the Rabbit*," Experimental Physiology, 1991, No. 76, pp. 125-134.

Serhan et al., "*Resolution of Inflammation: State of the Art, Definitions and Terms*," The FASEB Journal, vol. 21, Feb. 2007, pp. 325-332.

Moreland, "*Intra-Articular Hyaluronan (Hyaluronic Acid) and Hylans for the Treatment of Osteoarthritis: Mechanisms of Action*," University of Alabama at Birmingham, Arthritis Research & Therapy, vol. 5, No. 2, Jan. 2003, pp. 54-67.

Lee et al., "*Hyaluronan: A Multifunctional, MegaDalton, Stealth Molecule*," Current Opinion in Cell Biology, 2000, pp. 581-586.

Kalman et al., "*Effect of a Natural Extract of Chicken Combs with a High Content of Hyaluronic Acid (Hyal-Joint®) on Pain Relief and Quality of Life in Subjects with Knee Osteoarthritis: A Pilot Randomized Double-Blind Placebo-Controlled Trial*," Nutrition Journal, Jan. 2008, pp. 1-9.

Necas et al., "*Hyaluronic Acid (Hyaluronan): A Review*," Veterinarni Medicina, vol. 53, 2008, pp. 397-411.

Nishimoto et al., "*Effect of Chondroitin Sulfate and Hyaluronic Acid on Gene Expression in a Three-Dimensional Culture of Chondrocytes*," Journal of Bioscience and Bioengineering, vol. 100, No. 1, 2005, pp. 123-126.

Yamawaki et al., "*Hyaluronan Receptors Involved in Cytokine Induction in Monocytes*," Glycobiology, vol. 19, No. 1, 2009, pp. 83-92.

Lee et al., "*Production of Astaxanthin by Haematococcus*," Chemicals from Microalgae, Ed: Zvi Cohen, Taylor and Francis, UK (1999), pp. 173-195.

Bjerkeng et al., "*Bioavailability of all-E-astaxanthin and Z-isomers of Astaxanthin in Rainbow Trout (Oncorhynchus mykiss)*," Aquaculture, vol. 157, Issues 1-2, Nov. 1997, pp. 63-82; Abstract Only (2 pages).

Yang et al., "*Glioma-Associated Hyaluronan Induces Apoptosis in Dendritic Cells via Inducible Nitric Oxide Synthase: Implications for the use of Dendritic Cells for Therapy of Gliomas*," Cancer Res.; May 2002; 62(9):2583-91; Abstract Only (2 pages).

Ghosh et al., "*Potential Mechanism of Action of Intra-Articular Hyaluronan Therapy in Osteoarthritis: Are the Effects Molecular Weight Dependent?*" Semin Arthritis Rheum.; Aug. 2002; 32(1):10-37; Abstract Only (2 pages).

Rooney et al., "*Angiogenic Oligosaccharides of Hyaluronan Enhance the Production of Collagens by Endothelial Cells*," Journal of Cell Science; May 1993; 105 (Pt 1):213-218; Abstract Only (1 page).

Ruff et al., "*Eggshell Membrane in the Treatment of Pain and Stiffness from Osteoarthritis of the Knee: A Randomized, Multicenter, Double-blind, Placebo-Controlled Clinical Study*," Clinical Rheumatology, Aug. 2009; 28(8):907-14; Abstract Only (1 page).

Schiedt et al., "*Natural Occurrence of Enantiomeric and Meso-Astaxanthin, 5. Ex Wild Salmon (Salmo Salar and Oncorhynchus)*," Helv. Chim. Acta; 1981; 64(2):449-57; Abstract Only (1 page).

Jiang et al., "*Hyaluronan in Tissue Injury and Repair*," Annu Rev Cell Dev Biology; 2007; 23:435-61; Abstract Only (1 page).

Noble, "*Hyaluronan and its Catabolic Products in Tissue Injury and Repair*," Matrix Biology; Jan. 2002; 21(1):25-9; Abstract Only (1 page).

Stern et al., "*Hyaluronan Fragments: An Information-Rich System*," European Journal of Cell Biology; Aug. 2006; 85(8):699-715; Abstract Only (1 page).

Nir et al., "BioAstin Helps Relieve Pain and Improves Performance in Patients With Rheumatoid Arthritis," Health Research and Studies Center, Los Altos, California, Study Report, May 3, 2002, 8 pages.

\* cited by examiner

ASTAXANTHIN 3S, 3'S
(3,3'-DIHYDROXY-4,4'-DIKETO-β-CAROTENE)

COMPOSITION AND METHOD TO ALLEVIATE JOINT PAIN

RELATED APPLICATION(S)

This application is based upon prior filed provisional application Ser. No. 61/227,872, filed Jul. 23, 2009; and provisional application Ser. No. 61/345,652, filed May 18, 2010.

FIELD OF THE INVENTION

This invention relates to treating and alleviating symptoms of osteoarthritis and/or rheumatoid arthritis using therapeutic compositions and methods derived from krill extracts and/or marine oil compositions and synergistic additives.

BACKGROUND OF THE INVENTION

The use of krill and/or marine oil are disclosed in U.S. Patent Publication Nos. 2004/0234587; 2004/0241249; and 2007/0098808, the disclosures which are hereby incorporated by reference in their entirety. The beneficial aspects of using krill and/or marine oil are shown also in a research paper published by L. Deutsch as "Evaluation of the Effect of Neptune Krill Oil on Chronic Inflammation and Arthritic Symptoms," published in the Journal of the American College of Nutrition, Volume 26, No. 1, 39-49 (2007), the disclosure which is hereby incorporated by reference in its entirety.

The published '587, '249 and '808 applications discuss the beneficial aspects of using krill oil in association with pharmaceutically acceptable carriers. As an example, this krill and/or marine oil can be obtained by the combination of detailed steps as taught in the '808 application, by placing krill and/or marine material in a ketone solvent, separating the liquid and solid contents, recovering a first lipid rich fraction from the liquid contents by evaporation, placing the solid contents and organic solvent in an organic solvent of the type as taught in the specification, separating the liquid and solid contents, recovering a second lipid rich fraction by evaporation of the solvent from the liquid contents and recovering the solid contents. The resultant krill oil extract has also been used in an attempt to decrease lipid profiles in patients with hyperlipidemia. The '808 publication gives details regarding this krill oil as derived using those general steps identified above.

The published article gives further details of how the processed krill oil alone, at 3000 mgs/daily dose is a product that aids in treating chronic inflammation and arthritic symptoms. The article describes a study, which had several objectives: a) to evaluate the effect of Neptune Krill Oil on C-reactive protein (C-RP) on patients with chronic inflammation; and b) to evaluate the effectiveness of the Neptune Krill Oil on arthritic symptoms. The method used a randomized, double blind, placebo controlled study protocol. Ninety patients were recruited with either a confirmed diagnosis of cardiovascular disease and/or rheumatoid arthritis and/or osteoarthritis and with increased levels of CRP (>1.0 mg/dl) upon three consecutive weekly blood analysis prior to initiation of oral treatment with krill oil. It is important to note that C-RP is a well known biomarker for risk of cardiovascular disease, therefore in this trial, since patients with known cardiovascular disease states we not excluded from the trial the protocol appears to have evaluated the effects of krill oil on this cardiovascular risk factor while evaluating the effects of krill oil supplementation on the pain and discomfort associated with OA and RH. Group A received the Neptune Krill Oil (300 mg daily) and group B received a placebo. C-RP and Western Ontario and McMaster Universities (WOMAC) osteoarthritis scores were measured at baseline and days 7, 14 and 30. After seven days of treatment, the Neptune Krill Oil reduced CRP by 19.3% compared to an increase by 15.7% observed in the placebo group (p=0.049). After 14 and 30 days of treatment, the Neptune Krill Oil further decreased CRP by 29.7% and 30.9% respectively (p<0.001). The CRP levels of the placebo group increased to 32.1% after 14 days and then decreased to 25.1% at day 30. The between group difference was statistically significant; p=0.004 at day 14 and p=0.008 at day 30. The application of the processed Neptune Krill Oil showed a significant reduction in all three WOMAC scores. After seven days of treatment, the Neptune Krill Oil reduced pain scores by 28.9% (p=0.050), reduced stiffness by 20.3% (p=0.001) and reduced functional impairment by 22.8% (p=0.008). The results of that study indicate that the Neptune Krill Oil at a daily dose of about 300 mg significantly inhibits inflammation, reduces arthritic symptoms within a short treatment period of 7 and 14 days and may be effective in reducing the risk of cardiovascular disease by reduction of C-RP in the patient population employed.

SUMMARY OF THE INVENTION

In accordance with a non-limiting example, even more beneficial and synergistic effects for alleviating joint pain and symptoms of osteoarthritis and/or rheumatoid arthritis have been found when krill oil and/or marine oil are used in combination with other active constituents.

In accordance with a non-limiting example, the method treats and alleviates symptoms of osteoarthritis and/or rheumatoid arthritis in a patient by administering a therapeutic amount of a composition including a krill oil in combination with astaxanthin and low molecular weight polymers of hyaluronic acid or sodium hyaluronate (hyaluronan) in an oral dosage form. The krill oil in one example is derived from *Euphasia* spp., comprising Eicosapentaenoic (EPA) and Docosahexaenoic (DHA) fatty acids in the form of triacylglycerides and phospholipids, although not less than 1% EPA and 5% DHA has been found advantageous. In another example, the krill oil includes at least 15% EPA and 9% DHA, of which not less than 45% are in the form of phospholipids. The composition can be delivered advantageously for therapeutic results with 1-4000 mg of krill oil delivered per daily dose. In another example, 0.1-50 mg astaxanthin are supplemented to the krill oil per daily dose.

The astaxanthin is preferably derived from *Haematococcus pluvialis* algae, *Pfaffia*, krill, or by synthetic routes, in the free diol, monoester or diester form. These polymers of hyaluronic acid or sodium hyaluronate (hyaluronan) can be derived from microbial fermentation or animal tissue. About 1-500 mg of hyaluronan can be delivered per daily dose. The hyaluronan is micro- or nano-dispersed within the composition in one preferred example. In a preferred example, the hyaluronic acid is derived from a biofermenation process and has surprisingly a relatively low molecular weight between 0.5 and 100 kilodaltons (kDa). In another example, the polymers of hyaluronic acid or sodium hyaluronate (hyaluronan) are derived from animal tissue and have molecular weights exceeding 100 kDa. Such high molecular weight hyaluronans are typically derived from rooster combs and are reportedly mildly anti-inflammatory though this fact is somewhat controversial. The literature clearly indicates that as the molecular weight of hyaluroic acid and its salts increases, its immunogenicity drops dramatically. In addition, the scientific literature clearly points out that low molecular weight hyaluronic acids fragments are unexpectedly highly pro-inflammatory with respect to the innate immune system and would thus not be expected to useful in the treatment of inflammatory disease states and in particular joint pain associated with OA and/or RH.

The composition may also include a natural or synthetic cyclooxygenase-1 or -2 inhibitor comprising aspirin, acetaminophen, steroids, prednisone, or NSAIDs. The composition may also include a gamma-linoleic acid rich oil comprising Borage (*Borago officinalis* L.) or Safflower (*Carthamus tinctorius* L.).

The composition may also include an n-3 (omega-3) fatty acid rich oil derived from fish oil (EPA and DHA), algae oil (EPA and DHA), flax seed oil (ALA), perrila seed oil (ALA) or chia seed oil (ALA) and the n-3 fatty acid comprises, either alone or in combination, alpha-linolenic, stearidonic, eicosapentaenoic or docosapentaenoic acid. Soluble or insoluble forms of Collagen and elastin such as those derived from hydrolyzed or un-hydrolyzed eggshell membrane can also be added. The composition may also include anti-inflammatory and/or joint health promoting compounds comprising at least one of the preparations of the green lipped mussel (*Perna canaliculus*), *Boswellia serrata*, turmeric (*Curcuma longa*), stinging nettle (*Urtica dioica*), Andrographis, Cat's claw (*Uncaria tomentosa*), bromelain, methylsulfonylmethane (MSM), chondroitin sulfate, glucosamine sulfate, s-adenosyl-methionine, proanthocyanidins, procyanidins or flavonoids, and preparations of hydrolyzed or un-hydrolyzed eggshell membrane. The composition may include naturally-derived and synthetic antioxidants that are added to retard degradation of polyunsaturated fatty acids and/or the potent anti-oxidant astaxanthin.

Different compositions may use different ingredients in combination with the krill oil, astaxanthin and hyaluronate and be combined with different ingredients and supplemental compositions for more specific purposes.

A pharmaceutically acceptable composition comprises a krill oil in combination with astaxanthin and hyaluronate and optionally combined with glucosamine sulfate, chondroitin sulfate, collagen, methylsulfonmethane, a gamma-linoleic acid or omega-3 fatty acid rich oil or cyclooxygenase inhibitor for the treatment of symptoms related to joint pain or joint diseases including but not limited to osteoarthritis and rheumatoid arthritis.

In yet another example, a dietary supplement acceptable composition comprises a krill oil in combination with astaxanthin and hyaluronate and optionally combined with glucosamine sulfate, chondroitin sufate, collagen, methylsulfonmethane, a gamma-linoleic acid or omega-3 fatty acid rich oil and a cyclooxygenase inhibitor for the treatment of symptoms related to joint pain or joint diseases including but not limited to osteoarthritis and rheumatoid arthritis.

In yet another example, a medical food acceptable composition comprises a krill oil in combination with astaxanthin and hyaluronate and optionally combined with glucosamine sulfate, chondroitin sufate, collagen, methylsulfonmethane, a gamma-linoleic acid or omega-3 fatty acid rich oil and cyclooxygenase inhibitor for the treatment of symptoms related to joint pain or joint diseases including but not limited to osteoarthritis and rheumatoid arthritis.

In still another example, a composition is formulated in a therapeutic amount to treat and alleviate symptoms of osteoarthritis and/or rheumatoid arthritis, wherein the composition includes a krill oil in combination with astaxanthin and polymers of hyaluronic acid or sodium hyaluronate (hyaluronan) in an oral dosage form. This composition may include other active constituents as explained and identified above relative to the method and composition.

A process for extracting astaxanthin from *Haematococcus pluvialis* algal biomass is also disclosed and comprises providing a dried form of *Haematococcus pluvialis*, extracting astaxanthin using one of at least a polar and non polar solvent to obtain a slurry, filtering the slurry to separate the cells from the extract, and obtaining an astaxanthin oleoresin concentrate by removing solvent from the extract. This astaxanthin oleoresin concentrate is administered to a human patient in an oral dosage form containing 1 to 50 mg of astaxanthin oleoresin complex to treat and alleviate symptoms of osteoarthritis and/or rheumatoid arthritis in one example.

BRIEF DESCRIPTION OF THE DRAWINGS

Other objects, features and advantages of the present invention will become apparent from the detailed description of the invention which follows, when considered in light of the accompanying drawings in which.

DETAILED DESCRIPTION OF THE PREFERRED EMBODIMENTS

Figure 1:
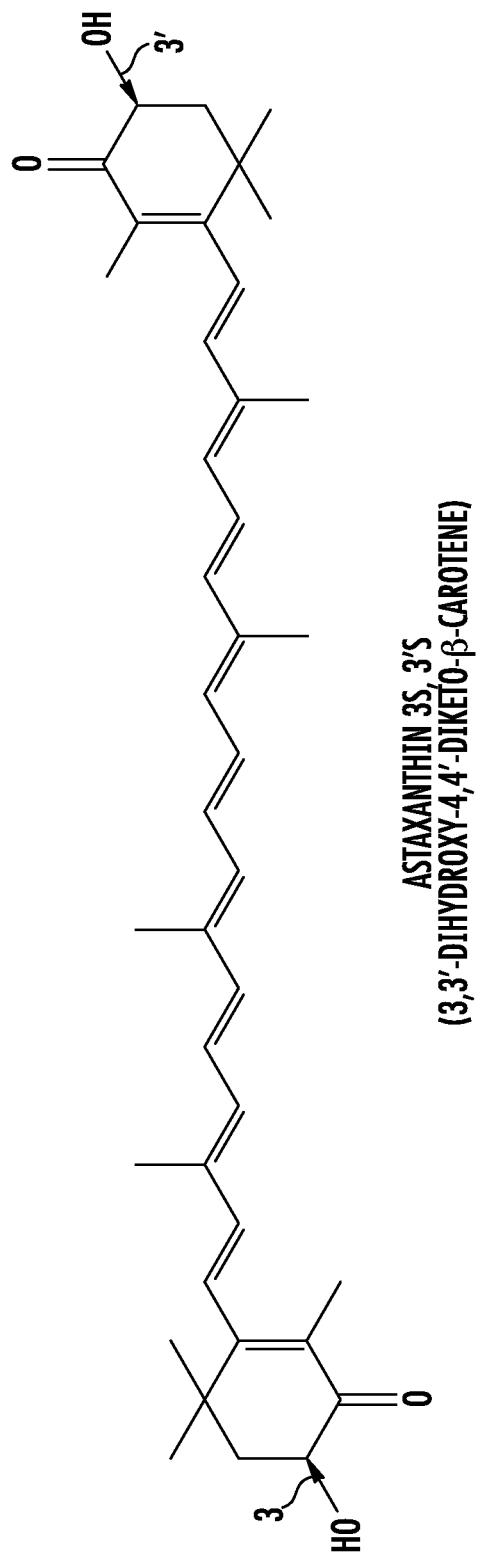
FIG. 1 is a view showing a chemical structure of astaxanthin that can be used in accordance with a non-limiting example.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The composition includes EPA and DHA functionalized as marine phospholipids and acyltriglycerides derived from krill and esterified astaxanthin, and in one non-limiting example, low molecular weight polymers of hyaluronic acid or sodium hyaluronate (hyaluronan) in an oral dosage form. Some of these components are explained in the following chart:

| Components | Percentage (%) |
|---|---|
| PHOSPHOLIPIDS | |
| PC, PE, PI, PS, SM, CL | >40 |
| OMEGA-3 (functionalized on PL) | >30 |
| Eicosapentaenoid Acid (EPA)* | >17 (15% in one example and 10% in another) |
| Docosahexaenoid Acid (DHA)+ | >11 (9% in one example and 5% in another) |
| ANTIOXIDANTS | (mg/100 g) |
| Astaxanthin, Vitamin A, Vitamin E | >1.25 |

\* > 55% of PL-EPA/Total EPA
+ > 55% of PL-DHA/Total DHA
These amounts can vary depending on application and persons.

As noted before, surprisingly the composition includes a pro-inflammatory low molecular weight Hyaluronic Acid (LMWtHA). Natural high molecular weight hyaluronic acid is the major hydrodynamic component of synovial fluid and importantly is known to be immuno-neutral to the innate immune system. It is nature's bone joint shock absorbent and lubricant. It has been found that there is excellent oral bioavailability of LMWtHA fragments specifically to connective tissue, which maximizes interaction with target synovial fluid producing cells. Therefore in a preferred composition containing krill oil, astaxanthin and LMWtHA, two anti-inflammatory components are thus combined with one highly inflammatory component. The scientific literature indicates that LMWtHA fragments exhibit potent pro-inflammatory behavior. It therefore remains unclear why a pro-inflammatory component would elicit a favorable overall response in inflamed joint tissues. It is believed that such pro-inflammatory LMWtHA fragments may promote site repair by simulation of the innate immune system repair mechanism and by simulating production of non-immunogenic high molecular weight HA bringing the joint back to homeostasis, however these are theories. A great deal of work by leading immunologists is still attempting to unravel all the aspects of the complicated singling processes associated with the innate immune system. Studies using large animal models of osteoarthritis have shown that mild immunogenic Hyaluronic Acids with molecular weights within the range of 0.5-1.0× $10^6$ Da (Dalton) were generally more effective in reducing indices of synovial inflammation and restoring the rheological properties of SF (visco-induction) than non-immunogenic HA's with molecular weights >2.3×$10^6$ Da.

Astaxanthin is a required component of the instant invention. Related scientific literature indicates that in a lipopolysaccharide induced inflammatory rat model, astaxanthin at just 1 mg/kg in vitro and in vivo: (1) down regulates TNF-alpha production by 75%; (2) down regulates prostaglandin E-2 production (PGE-2) by 75%; (3) inhibits nitric oxide synthase (NOS) expression of nitric oxide by 58%; and (4) these effects on inflammatory markers were nearly as effective as prednisolone in this model. FIG. 1 shows an example of the astaxanthin as astaxanthin 3S, 3'S (3, 3'-dihydroxy-4, 4'-diketo-β-carotene). Such information suggests but does not prove that astaxanthin may be an effective standalone product for the reduction of OA and/or RH pain or other symptomology associated with OA and/or RH.

In induced uveitis, astaxanthin also showed dose dependant ocular anti-inflammatory activity by suppression of NO, PGE-2 and TNF-Alpha by directly blocking NO synthase activity. Astaxanthin is also known to reduce C-Reactive Protein (C-RP) blood levels in vivo. For example, in human subjects with high risk levels of C-RP three months of astaxanthin treatment resulted in 43% of patients serum C-RP levels to drop below the risk level. This may explain why C-RP levels dropped significantly in the Deutsch study. Astaxanthin is so powerful that it has been shown to negate the pro-oxidant activity of Vioxx, a COX-2 inhibitor belonging to the NSAIDS drug class which is known to cause cellular membrane lipid per-oxidation leading to heart attack and stroke. For this reason Vioxx was removed from the US market. Astaxanthin is absorbed in vitro by lens epithelial cells where it suppresses UVB induced lipid per-oxidative mediated cell damage at umol/L concentrations. In human trials astaxanthin at 4 mgs/day prevented post exercise joint fatigue following strenuous knee exercise when compared to untreated subjects. These results have been shown in:
1) Lee et al., Molecules and Cells, 16(1):97-105; 2003;
2) Ohgami et al., Investigative Ophthalmology and Visual Science 44(6):2694-2701, 2003;
3) Spiller et al., J. of the Amer. College of Nutrition, 21(5): October 2002; and
4) Fry et al., Univ. of Memphis Human Performance Laboratories, 2001 and 2004, Reports 1 & 2.

A preferred composition in one embodiment includes 300 mg of krill oil, 45 mg of low molecular weight HA, and 2 mg astaxanthin.

Astaxanthin has potent singlet oxygen quenching activity. Astaxanthin typically does not exhibit pro-oxidant activity unlike β-carotene, lutein, zeaxanthin and Vitamins A and E. Astaxanthin in some studies has been found to be about 50 times more powerful than Vitamin E, 11 times more powerful than β-carotene and three times more powerful than lutein in quenching of singlet oxygen. Astaxanthin is also well known for its ability to quench free radicals. Comparative studies have found astaxanthin to be 65 times more powerful than Vitamin C, 54 times more powerful than β-carotene, 47 times more powerful than lutein, and 14 times more powerful than Vitamin E in free radical quenching ability.

U.S. Pat. No. 5,527,533 (the Tso patent), the disclosure which is hereby incorporated by reference in its entirety, discloses the benefits of astaxanthin for retarding and ameliorating central nervous system and eye damage. Astaxanthin crosses the blood-brain-retina barrier and this can be measured by direct measurement of retinal astaxanthin concentrations. Thus, Tso demonstrated protection from photon induced damage of photo-receptors, ganglion and neuronal cell damage.

Studies have shown that HA binds to the surface of dendritic cells ("DC's") and stimulated T-cells. Blockade of the CD44-HA interaction leads to impaired T-Cell activation both in vitro and in vivo. Studies have shown that in cancer cell lines, LMWtHA fragments specifically induce nitric oxide synthase in dendritic cells. In DC's, NO expression caused dendritic cell apoptosis (cell death). DC's are essential T-cell activators which function by presenting antigens to T-cells, thus apoptosis of DC's may short circuit the adaptive immune system response. This effect was clearly CD44 dependent because pretreatment of DC's with anti-CD44 monoclonal antibodies blocked the NO mediated induction of DC apoptosis. It appears that low molecular weight HA fragments interrupt the normal course of the well known T-cell mediated adaptive immune system response. CD44 is a glycoprotein responsible in part for lymphocyte activation (also known as T-cell activation) and is known to specifically bind to HA. On the other hand as previously discussed low molecular weight HA fragments appear to up-regulate the innate immune response, particularly in chronic inflammatory conditions where the innate immune system may in some way be compromised.

Support for such teachings can be found in:
1) Mummert et al., J. of Immunol. 169, 4322-4331;
2) Termeer et al., Trends in Immunology, Vol. 24, March 2003;
3) Yang et al., Cancer Res. 62, 2583-2591; and
4) KcKee et al., J. Biol. Chem. 272, 8013-8018.

Additional information can be found in the following references: Ghosh P. Guidolin D. Semin Arthritis Rheum., 2002 August; 32(1):10-37; and P. Rooney, M. Wang, P. Kumar and S. Kumar, Journal of Cell Science 105, 213-218 (1993).

As noted before, krill oil is typically produced from Antarctic krill (*Euphausia superba*), which is a zooplankton (base of food chain). It is one of the most abundant marine biomass of about 500 million tons according to some estimates. Antarctic krill breeds in the pure uncontaminated deep sea waters. It is a non-exploited marine biomass and the catch per year is less than or equal to about 0.02% according to some estimates.

It is believed that Krill oil based phospholipid bound EPA and DHA uptake into cellular membranes is far more efficient than triacylglyercide bound EPA and DHA since liver conversion of triacylglycerides is itself inefficient and because phospholipid bound EPA and DHA can be transported into the blood stream via the lymphatic system, thus, avoiding liver breakdown. In addition, krill oil consumption does not produce the burp-back observed with fish oil based products. Because of this burp-back feature of fish oils, it has been found that approximately 50% of all consumers who try fish oil never buy it again.

Astaxanthin has an excellent safety record. A conducted study obtained the results as follows:
  Oral LD 50: 600 mg/kg (rats);
  NOAEL: 465 mg/kg (rats); or
  Serum Pharmacokinetics: Stewart et al. 2008
  1) $T_{1/2}$: 16 hours;
  2) $T_{max}$: 8 hours;
  3) $C_{max}$: 65 µg/L.

At eight weeks of supplementation at 6 mg per day, there was no negative effect in healthy adults. Spiller et al. 2003.

In accordance with one non-limiting example, astaxanthin has three prime sources. 3 mg astaxanthin per 240 g serving of non-farmed raised salmon or a 1% to 12% astaxanthin oleoresin or 1.5-2.5% beadlet derived from microalgae. Further verification is reflected in Lee et al., Molecules and Cells 16(1): 97-105, 2003; Ohgami et al., Investigative Ophthalmology and Visual Science 44(6): 2694-2701, 2003; Spiller et al., J. of the American College of Nutrition 21(5): October 2002; and Fry et al., University of Memphis, Human Performance Laboratories, 2001 and 2004, Reports 1 and 2.

Although many beneficial and synergistic effects are now being reported herein have been observed when krill oil is used in combination with other active ingredients, and more particularly, krill oil in combination with astaxanthin and polymers of hyaluronic acid or sodium hyaluronate in preferably an oral dosage form for the control of joint pain range of motion and stiffness, it should be understood that different proportions of ingredients and percentages in compositions can be used depending on end use applications and other environmental and physiological factors when treating a patient.

In accordance with a non-limiting example, the method treats and alleviates symptoms of osteoarthritis and/or rheumatoid arthritis in a patient by administering a therapeutic amount of a composition including a krill oil in combination with astaxanthin and polymers of hyaluronic acid or sodium hyaluronate (hyaluronan) in an oral dosage form. The krill oil in one example is derived from *Euphasia* spp., comprising Eicosapentaenoic (EPA) and Docosahexaenoic (DHA) fatty acids in the form of triacylglycerides and phospholipids, although not less than 1% EPA and 5% DHA has been found advantageous. In another example, the krill oil includes at least 15% EPA and 9% DHA, of which not less than 45% are in the form of phospholipids. The composition can be delivered advantageously for therapeutic results with 1-4000 mg of krill oil delivered per daily dose. In another example, 0.1-50 mg astaxanthin are supplemented to the krill oil per daily dose.

The astaxanthin is preferably derived from *Haematococcus pluvialis* algae, *Pfaffia*, krill, or by synthetic routes, in the free dial, monoester or diester form at a daily dose of 0.5-8 mg. The polymers of hyaluronic acid or sodium hyaluronate (hyaluronan) can be derived from microbial fermentation or animal tissue. About 1-500 mg of hyaluronan can be delivered per daily dose and preferably between 10 and 70 mgs/dose. The hyaluronan is micro- or nano-dispersed within the composition in one preferred example. In another example, the hyaluronic acid is derived from a bio-fermenation process and has a molecular weight between 0.5 and 100 kilodaltons (kDa). In another example, the polymers of hyaluronic acid or sodium hyaluronate (hyaluronan) are derived from microbial fermentation or animal tissue and have molecular weights exceeding 100 KDa and preferably up to $10^6$ KDa.

The composition may also include a natural or synthetic cyclooxygenase-1 or -2 inhibitor comprising for example aspirin, acetaminophen, steroids, prednisone, or NSAIDs. The composition may also include a gamma-linoleic acid rich oil comprising Borage (*Borago officinalis* L.) or Safflower (*Carthamus tinctorius* L.), which delivers a metabolic precursor to $PGE_1$ synthesis.

The composition may also include an n-3 (omega-3) fatty acid rich oil derived from fish oil, algae oil, flax seed oil, or chia seed oil and the n-3 fatty acid comprises alpha-linolenic, stearidonic, eicosapentaenoic or docosapentaenoic acid. Hydrolyzed or unhydrolyzed collagen and elastin derived from eggshell membranes can also be advantageously added. The composition may also include anti-inflammatory and/or natural joint health promoting compounds comprising at least one of preparations of green lipped mussel (*Perna canaliculus*), *Boswellia serrata*, turmeric (*Curcuma longa*), stinging nettle (*Urtica dioica*), Andrographis, Cat's claw (*Uncaria tomentosa*), bromelain, methylsulfonylmethane (MSM), chondroitin sulfate, glucosamine sulfate, s-adenosyl-methionine, proanthocyanidins, procyanidins or flavonoids. The composition may include naturally-derived and synthetic antioxidants that are added to retard degradation of fatty acids and astaxanthin.

Different compositions may use different ingredients in combination with the krill oil, astaxanthin and hyaluronate and be combined with different ingredients and supplemental compositions for more specific purposes.

A pharmaceutically acceptable composition comprises a krill oil in combination with astaxanthin and hyaluronate optionally combined with one or more ingredients including but not limited to glucosamine sulfate, chondroitin sulfate, collagen, methylsulfonmethane, a gamma-linoleic acid or omega-3 fatty acid rich oil a cyclooxygenase inhibitor or a lipogenase inhibitor for the treatment of symptoms related to joint diseases including but not limited to osteoarthritis and rheumatoid arthritis.

In yet another example, a dietary supplement acceptable composition comprises a krill oil in combination with astaxanthin and hyaluronate optionally combined one or more ingredients, including but not limited to, glucosamine sulfate, chondroitin sufate, collagen, methylsulfonmethane, a gamma-linoleic acid or omega-3 fatty acid rich oil a cyclooxygenase inhibitor or a lipoxygenase inhibitor for the treatment of symptoms related to joint diseases including but not limited to osteoarthritis and rheumatoid arthritis.

In yet another example, a medical food acceptable composition comprises a krill oil in combination with astaxanthin and hyaluronate and optionally combined with one or more ingredients including glucosamine sulfate, chondroitin sufate, collagen, methylsulfonmethane, a gamma-linoleic acid or omega-3 fatty acid rich oil, a cyclooxygenase inhibitor or a lipoxygenase inhibitor for the treatment of symptoms related to joint diseases including but not limited to osteoarthritis and rheumatoid arthritis.

In still another example, a composition is formulated in a therapeutic amount to treat and alleviate symptoms of osteoarthritis and/or rheumatoid arthritis, wherein the composition includes a krill oil in combination with astaxanthin and polymers of hyaluronic acid or sodium hyaluronate (hyaluronan) in an oral dosage form. This composition includes other active constituents as explained and identified above relative to the method and composition.

A process for extracting astaxanthin from *Haematococcus pluvialis* algal biomass is also disclosed and comprises providing a dried form of *Haematococcus pluvialis*, extracting astaxanthin using one of at least a polar and non polar solvent to obtain a slurry, filtering the slurry to separate the cells from the extract, and obtaining an astaxanthin oleoresin concentrate by removing solvent from the extract. This astaxanthin oleoresin concentrate is administered to a human patient in an oral dosage form containing 1 to 50 mg of astaxanthin oleoresin complex to treat and alleviate symptoms of osteoarthritis and/or rheumatoid arthritis in one example.

Other details of the type of CO2 extraction and processing technology (as supercritical CO2 extraction) and peroxidation blocker technology that can be used are disclosed in commonly assigned U.S. Patent Publication Nos. 2009/0181127; 2009/0181114; and 2009/0258081, the disclosures which are hereby incorporated by reference in their entirety.

There now follows further details of an astaxanthin extract that can be formed from *Haematococcus pluvialis* and an associated method for preparation thereof. As described below, this astaxanthin extract and method advantageously can be used alone in an oral dosage form to treat and alleviate symptoms of osteoarthritis and/or rheumatoid arthritis. It is also applied in combination with krill oil and LMWtHA as described above.

In this example, astaxanthin oleoresin complex is derived from alga *Haematococcus pluvialis*, wherein the astaxanthin oleoresin complex is useful for relieving pain in Osteoarthritic patients.

It should be understood that application of astaxanthin from the algae *Haematococcus pluvialis* for the improvement of muscle function, muscle disorders, muscle diseases and carpal tunnel syndrome are reported. In these many studies, astaxanthin oleoresin extracted through super critical CO2 extraction was used. However, no studies or clinical trials were carried out using astaxanthin oleoresin specifically for alleviating symptoms of Osteoarthritis.

Osteoarthritis (OA) is the most prevalent form of arthritis. Osteoarthritis is a disease in which the cartilage that acts as a cushion between the bones in joints begins to wear away causing bone on bone joint swelling and joint pain. It is characterized by degeneration of articular cartilage along with peri-articular bone response. It affects both sexes, mainly in the fourth and fifth decades of life. The knee joint is most commonly affected joint. At present the management is by pharmacological and non-pharmacological therapy. Corrective surgical therapy and or joint replacement therapy in some cases may not be possible.

Traditional treatments for Osteoarthritis involve the use of analgesics, non-steroidal anti-inflammatory drugs (NSAIDs) or cyclooxygenase-2 specific (COX-2) NSAIDs alone or in combination. Advances in recombinant protein synthesis also provide relief from the symptoms of OA and RH. Steroid or high molecular weight hyaluronic acid injections have also been used with some success however these therapies have well known deleterious side effects.

Many of these treatments alone have shown limited effectiveness in clinical trials. To avoid the cardiac risks and gastrointestinal issues associated with traditional OA treatments (particularly with long term use), many patients have turned to complimentary and alternative medicines (CAMs) such as dietary supplements. Glucosamine and chondroitin alone or in combination, are widely marketed as dietary supplements to treat joint pain due to OA. Two major clinical trials on glucosamine and chondroitin (The GAIT Study) failed to show any significant improvement in WOMAC score over placebo except in the highest quartile of patients studied. Because of their limited effectiveness, the search for additional CAMs to treat OA continues (see for example Ruff et al., Eggshell membrane in the treatment of pain and stiffness from Osteoarthritis of the knee: a randomized, multicenter, double-blind, placebo-controlled clinical study, Clin. Rheumatol (2009) 28:907-914).

In accordance with a non-limiting example, a composition comprises astaxanthin oleoresin complex derived form *Haematococcus pluvialis* algal biomass as a single component treatment to relieve the symptoms of OA. A process for extraction of the astaxanthin oleoresin complex from alga *Haematococcus pluvialis* is also provided. A use of the astaxanthin oleoresin complex is provided wherein the astaxanthin oleoresin complex is useful for relieving pain in Osteoarthritis patients when administered in an effective amount. The astaxanthin oleoresin complex as disclosed is helpful in improving the quality of life, functionality and by administering required amount of Astaxanthin oleoresin complex.

The astaxanthin oleoresin complex as disclosed is derived by extraction of the *Haematococcus pluvialis* algal biomass by solvent extraction using polar/non-polar solvents in a non-limiting example. The *Haematococcus pluvialis* biomass is obtained from cultivating the alga in open ponds, harvesting astaxanthin rich biomass, drying the harvested biomass to remove the moisture and cracking the dried biomass for extraction of astaxanthin complex from the said algal biomass.

The subject matter relates to long term management of the patients with Osteoarthritis in terms of a) relief of pain and b) improved functions of daily life using astaxanthin oleoresin complex as disclosed.

In one of embodiment, there is provided a composition comprising astaxanthin oleoresin complex. In another embodiment, there is provided a composition comprising the astaxanthin oleoresin complex derived from *Haematococcus pluvialis* algal biomass. In another embodiment, there is provided a process for extraction of astaxanthin from *Haematococcus pluvialis* algal biomass, wherein the process comprises providing dried form of *Haematococcus pluvialis*, extracting astaxanthin using polar and/or non-polar solvents to obtain a slurry; filtering the slurry to separate the cells from extract; and obtaining astaxanthin oleoresin concentrate by removing solvent from the extract. In another embodiment, there is provided *Haematococcus pluvialis* alga, wherein the alga is cultivated in open ponds or in closed photobioreactors. One embodiment provides the process for extraction of astaxanthin *Haematococcus pluvialis* algal biomass, wherein the *Haematococcus* alga accumulated with astaxanthin is harvested to concentrate the biomass. In another embodiment, there is provided a process for extraction of astaxanthin *Haematococcus pluvialis* algal biomass, wherein red cysts of the *Haematococcus pluvialis* are dried to remove the moisture. In another embodiment, there is provided a process for extraction of astaxanthin *Haematococcus pluvialis* algal biomass, wherein red cysts of the *Haematococcus pluvialis* are dried to remove the moisture and the dried red cysts are cracked for optimal extraction of the astaxanthin. A method improves the quality of life and functionality of Osteoarthritis patients by administering required amounts of astaxanthin oleoresin complex in oral dosage form.

In one embodiment, there is provided a method of improving the quality of life and functionality of Osteoarthritis patients by administering astaxanthin oleoresin complex in oral dosage forms containing 1-50 mg astaxanthin oleoresin complex. In another embodiment, there is provided a method of improving the quality of life and functionality of Osteoarthritis patients by administering astaxanthin oleoresin complex in oral dosage forms containing 1-30 mg astaxanthin oleoresin complex. In another embodiment, there is provided a method of improving the quality of life and functionality of Osteoarthritis patients by administering astaxanthin oleoresin complex in oral dosage forms containing 1-20 mg astaxanthin oleoresin complex. In another embodiment, there is provided a method of improving the quality of life and functionality of Osteoarthritis patients by administering astaxanthin oleoresin complex in oral dosage forms containing 10-25 mg astaxanthin oleoresin complex. In one embodiment, there is provided a method of improving the quality of life and functionality of Osteoarthritis patients by administering astaxanthin oleoresin complex in oral dosage forms containing 15 mg astaxanthin oleoresin complex. In another embodiment, there is provided a method of improving the quality of life and functionality of Osteoarthritis patients by administering astaxanthin oleoresin complex in oral dosage forms containing 3-8 mg, preferably 4 mg, most preferably 5 mg astaxanthin oleoresin complex. In another embodiment, there is provided a method of improving the quality of life and functionality of Osteoarthritis patients by administering astaxanthin oleoresin complex in oral dosage forms containing astaxanthin oleoresin complex, wherein the Osteoarthritis assessment in Osteoarthritis patients is based on Western Ontario and McMasters Universities (WOMAC) Osteoarthritis Index.

In one of the embodiment, there is provided a dietary supplement formulation comprising astaxanthin oleoresin complex, either alone or in conjunction with surfactants to improve the absorption of astaxanthin and therefore the bio-availability of astaxanthin wherein the formulation is useful for improving the quality of life, functionality and relief of pain in Osteoarthritis, wherein the formulation comprises 1-50 mg astaxanthin oleoresin complex. In another embodiment, there is provided a pharmaceutical formulation comprising astaxanthin oleoresin complex, either alone or in conjunction with surfactants to improve the absorption of astaxanthin and therefore the bio-availability of astaxanthin, wherein the formulation is useful for improving the quality of life, functionality and relief of pain in Osteoarthritis, wherein the formulation comprises 1-50 mg astaxanthin oleoresin complex. In yet another embodiment, there is provided a food product comprising astaxanthin for improving the quality of life, functionality and relief of pain in Osteoarthritis, wherein the formulation comprises 1-50 mg astaxanthin oleoresin complex either alone or in conjunction with surfactants to improve the absorption of astaxanthin and therefore the bio-availability of astaxanthin. In yet another embodiment, there is provided food and/or beverage product comprising astaxanthin oleoresin complex either alone or in conjunction with surfactants to improve the absorption of astaxanthin and therefore the bio-availability of astaxanthin for improving quality of life, functionality and relief of pain in Osteoarthritis, wherein the formulation comprises 1-50 mg astaxanthin oleoresin complex. One embodiment provides the astaxanthin formulations as disclosed comprising 2 to 20 mg of astaxanthin.

Cultivation of *Haematococcus pluvialis* Alga

*Haematococcus* is a uni-cellular green microalga which has the capacity to concentrate in its cells the xanthophyll/carotenoid pigment astaxanthin under appropriate growth conditions. Astaxanthin has a characteristic red color. *Haematococcus* alga can concentrate astaxanthin up to 1.0% to 2% of its body weight in open pond cultivation or up to 5% in photobioreactors. The alga is grown in open ponds containing water enriched with nutrients of nitrates, phosphate, magnesium, $CO_2$, minerals etc., for the algal growth. The cultivation of the alga is not a continuous process and is carried out under a batch process of 7-10 days.

The Astaxanthin rich alga is separated/harvested using mechanical methods/separator machines from the pond culture medium and the filtrate from the pond is cleaned and recycled. The harvested algal slurry is washed using fresh water and concentrated. Thereafter the slurry in wet form along with antioxidants is dried through a spray drier. The powder is stored under normal warehouse condition and or in cold storage and then cracked and stored under nitrogen or vacuum packed. An example is given in Indian Patent No. 201526 (Swati S Thomas, Kumaravel S and Jeeji Bai N—2003—A cyclic process for the production of astaxanthin enriched biomass from *Haematococcus* algae) on "A cyclic process for the production of astaxanthin enriched biomass from *Haematococcus* algae."

Extraction Process for the Preparation of Astaxanthin Oleoresin Complex

The dried form of *Haematococcus pluvialis* alga is used as the raw material for the extraction process. The algal powder is cracked using a cracking mill. The cracked cells are then immersed in a suitable polar/non-polar solvent and mixed. After giving sufficient time for astaxanthin extraction, the mixture is passed through a filtration unit to separate the cells from the extract. The spent cell with solvent is then passed through a unit to remove solvent from the cells. The clear filtrate with astaxanthin is then passed through a distillation unit to remove the solvent. The concentrated astaxanthin is finally passed through high vacuum distillation unit to strip the extraction solvent residue below 100 ppm level. All the operations are carried out under vacuum or under nitrogen atmosphere to avoid any degradation. Astaxanthin oleoresin is red in color and the concentration of astaxanthin will range from 2.5% to 10% depending on the level of astaxanthin in the algal powder.

Composition of *Haematococcus pluvialis* Cell Powder & Astaxanthin Oleoresin Complex Astaxanthin (3, 3'-dihydroxy-b, b-carotene-4, 4'-dione) is widely distributed in nature and is the principle pigment in crustaceans and Salmonoids, various birds including flamingos and scarlet ibis. The carotenoids impart distinctive orange red coloration (Bjørn Bjerkeng, Marianne Føllingb, Stephen Lagockia, Trond Storebakkena, Jan Ollic and Niels Alstedd. Bioavailability of all-Eastaxanthin and Z-isomers of astaxanthin in rainbow trout (*Oncorhynchus mykiss*). Aquaculture, (1997). 157: 63-82.

Astaxanthin is a keto (oxygenated) carotenoid with the molecular formula $C_{40}H_{52}O_4$ and has a molecular weight of 596.86. Astaxanthin exists in several stereochemical forms viz 3S, 3'S; 3R, 3'R; 3S, 3'R and 3R, 3'S depending on the source (Schiedt, K., Leuenberger, F. J., Vecchi, M. Analysis of astaxanthin as found in wild salmon and synthetic astaxanthin, Helv. Chim. Acta (1981) 64: 449-457). The major natural sources of astaxanthin include algae *Haematococcus*, yeast Phaffia and Krill apart from salmon and trout. Among these, *Haematococcus* is the richest source producing between 1% to 4% astaxanthin of its dry weight (Maher, T. J. Astaxanthin: A versatile carotenoid antioxidant. International Journal of Integrative Medicine (2000) Volume 2 (number 4)). In *Haematococcus* algae astaxanthin exists as 3S, 3'S isomer, whereas in the yeast it is in the form of 3R, 3'R isomer. Astaxanthin exists in *Haematococcus* cells in the form of monoester and diester, which accounts for more then 90% of total astaxanthin. Other carotenoids such as beta-carotene, canthaxanthin and lutein are present in minor amounts (Lee, Y-K., Zhang, and D. H. Production of astaxanthin by *Haematococcus. In: Chemicals from Microalgae. Ed: Zvi Cohen, Taylor and Francis, UK (1999). Pp. 173-195). Astaxanthin exists in free form in synthetic astaxanthin and Phaffia yeast. The summary of results is given Table 1 and 2.

Clinical Trial to Evaluate the Efficacy of *Haematococcus pluvialis* Astaxanthin Oleoresin Complex in Osteoarthritis Patients The study has been carried out as a comparative single blind clinical trial of astaxanthin oleoresin complex in 60 Osteoarthritis patients as compared with Placebo control for a period of 12 weeks n=60 (30A+30 P). The dosage consisted of one softgel containing 15 mg of Astaxanthin once a day during breakfast for 12 weeks. A total of 70 subjects were recruited for the study, 35 in each group (Astaxanthin oleoresin complex and placebo-control) of both the sexes. Patients were explained the nature of the study and informed consent was obtained prior to the start of the study. Patient subjects were clinically examined by the Principal Investigator and team. X ray and blood samples were drawn at the commencement and at the end of study period. The case record forms were filled by the Principal Investigator and rechecked by the Clinical research associate. Sixty patient subjects completed the study. Ten were drop outs due to various reasons but not on account of intolerance to the astaxanthin oleoresin complex or placebo control. The results were tabulated by the expert data entry operators under supervision of Biometric expert. The results were subjected to Statistical analysis by an independent analyst.

The assessment of Osteoarthritis symptoms were based on Western Ontario and McMasters Universities (WOMAC) Osteoarthritis Index, VAS scale, Lequesne's functional scale as well as Sleep score as additional parameters besides radiological investigations. Further the assessment of Osteoarthritis symptoms based on haematological studies, specifically MMP3 (Matrix metalloproteinase 3) in clinical parameters since Osteoarthritis patients show elevated levels of MMP3 in blood as well as in synovial fluid. The elevated levels cause significant tissue damage through cartilage destruction.

Results of Clinical Trial and Discussions

Total Health Assessment Score

The total health assessment on Osteoarthritis patients was carried out on their difficulty to a) Dressing—doing buttons, washing and combing hair b) Arising—stand up straight from a chair, get in and out of bed, sit cross-legged on floor and get up c) Eating—cut vegetables, lift a full cup/glass to your mouth d) Walking—walk outdoor on flat ground, climb up five steps and e) Hygiene—Take a bath, wash and dry your body, get on and off the toilet f) Reaching—reach and get down a 2 kg object from just above your head, bend down to pick up clothing from the floor g) Grip—open a bottle previously opened, turn taps on & off, open door latches h) Activities—work in office/house, run errand to shop, get in and out of car/auto. The summary of results is given Table 3.

There were significant reductions in the mean scores of patients taking astaxanthin oleoresin complex at the end of 3 months but not for the Placebo group. There were no significant differences between astaxanthin and Placebo group at Basal values. There were significant differences between the astaxanthin and placebo group at 3 months.

WOMAC Score

The Western Ontario McMaster (WOMAC) is a validated instrument designed specifically for the assessment of lower extremity pain and function in Osteoarthritis (OA) of the knee. The patients were assessed on their pain, stiffness and difficulty in carrying out day-to-day activities. The pain index was assessed for Activities—a) in walking on flat surface, going up or down on flat surface, at night while in bed, sitting or lying, standing upright b) Stiffness—after first wakening in morning, after sitting/lying or resting later in the day and c) difficulty in descending stairs, ascending stairs, standing up from a chair, while standing, bending to floor to pick up objects, walking on flat ground, getting in & out of autorickshaw/bus/car, going shopping, on rising from bed, while lying on bed, while sitting on chair, going on/off toilet, doing heavy domestic duties such as moving heavy boxes/scrubbing floor/lifting shopping bags, doing light domestic duties such as cleaning room/table/cooking/dusting, while sitting cross-legged position, rising from cross-legged position, while squatting on floor. The summary of the results are given in Table 4.

There were significant reductions in the mean scores for patients taking Astaxanthin oleoresin complex at the end of 3 months but not for the Placebo group. There were no significant differences between patients taking Astaxanthin oleoresin complex and placebo group at basal values. There were significant differences between Astaxanthin and Placebo groups at 3 months.

VAS (Visual Analog Scale) on Pain Parameters

Pain parameters were assessed in Osteoarthritis patients taking astaxanthin oleoresin and the Placebo group using VAS. The assessment was carried out in a) Pain parameters—pain while using stairs, pain while walking on flat ground, pain while standing upright, pain while sitting or lying down, pain at night in bed b) Physical functions—going downstairs, going upstairs, sitting, getting up from sitting, standing, bending to floor, walking on flat ground, getting into or out of automobiles, shopping, putting on socks/stockings, taking off socks/stockings, getting into bed, getting out of bed, getting into or out of bath tub, getting on or off toilet seat, during heavy household chores, during light household chores, getting into lotus position. The summary of results of Pain parameters (Pain+Physical) scores are given in Table 5.

There were significant reductions in the mean scores at the end of 3 months for patients taking Astaxanthin oleoresin complex but not for the Placebo group. There were no significant differences between Astaxanthin oleoresin complex and Placebo group at Basal values. There were significant differences between Astaxanthin oleoresin complex and Placebo groups at 3 months.

Laquesne's Index

Laquesne's index is the Functional index for Osteoarthritis of the knee. Assessment is carried out on a) Pain/discomfort—during nocturnal bed rest, morning stiffness or regressive pain after rising, after standing for 30 minutes and b) Physical functions—maximum distance walked, activities of daily living like able to climb up a standard flight of stairs, able to climb down a standard flight of stairs, able to squat or bend on the knees, able to walk on uneven ground. The Laquesne's index results are given in Table 6.

There were significant reductions in mean scores for the patients taking Astaxanthin oleoresin complex at the end of 3 months but not for the Placebo group. There were no significant differences between astaxanthin oleoresin complex and Placebo groups at Basal values. There were significant differences between astaxanthin oleoresin complex and Placebo groups at 3 months.

Sleep Scale

Sleep is an important element of functioning and well being. Sleep Scale was originally developed in the Medical Outcomes Study (MOS) intended to assess the extent of sleep problems. The Medical Outcomes Study Sleep Scale includes 12 items assessing sleep disturbance, sleep adequacy, somnolence, quantity of sleep, snoring, and awakening short of breath or with a headache. A sleep problems index, grouping items from each of the former domains, is also available. This assessment evaluated the psychometric properties of MOS-Sleep Scale in Osteoarthritis patients taking Astaxanthin oleoresin complex and Placebo group. The results on Sleep scale MOS is given in Table 7.

There were significant reductions in the mean scores for patients taking astaxanthin oleoresin complex at the end of 3 months but not for the Placebo group. There were no significant differences between astaxanthin oleoresin complex group and Placebo group at Basal values. There were significant differences between astaxanthin oleoresin complex group and Placebo group for most of the variables.

MMP3 (Matrix Metalloproteinase 3) Assay

Figure 2:
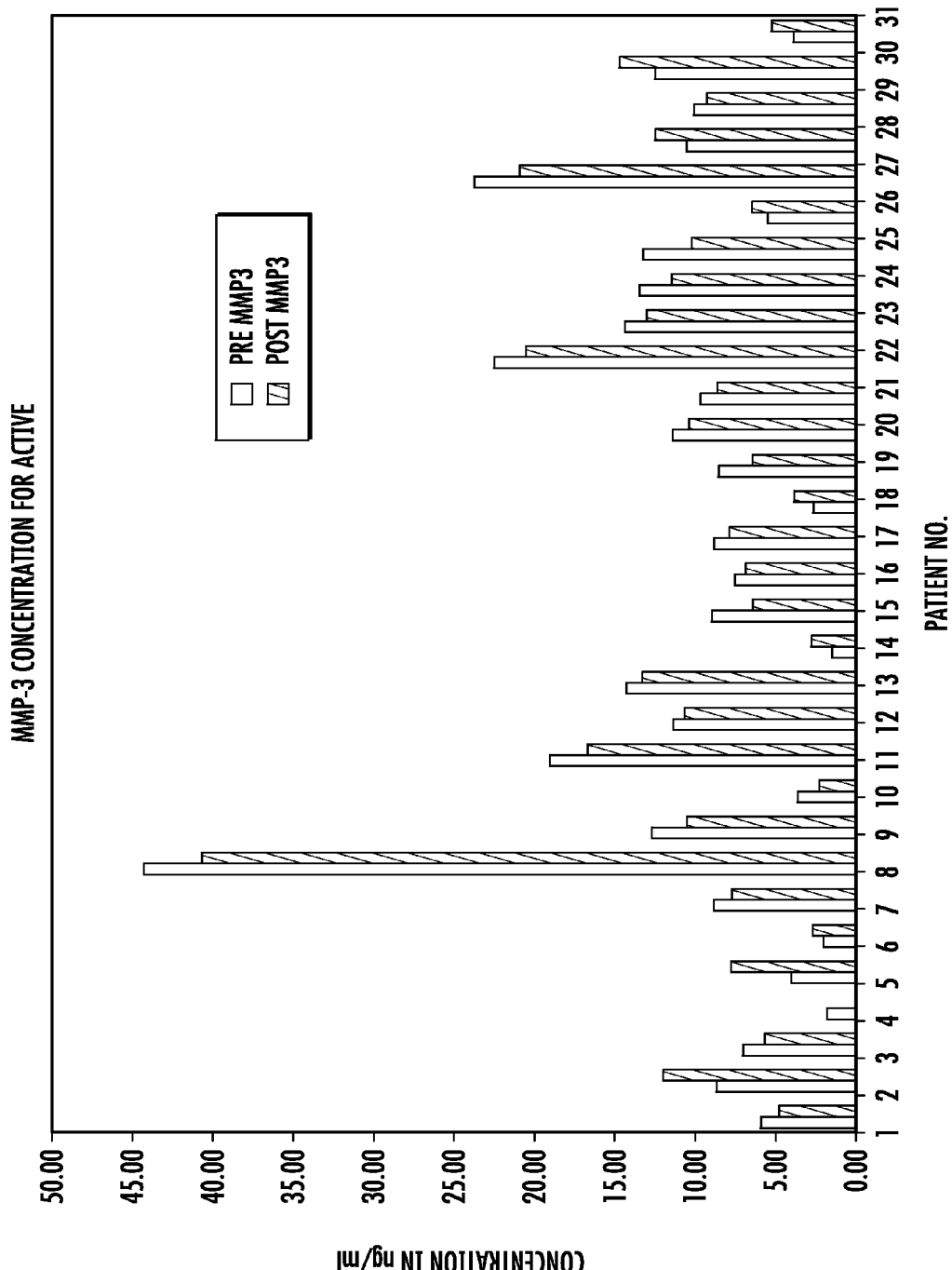
FIG. 2 shows the MMP3 concentration in osteoarthritis (OA) patients administered with an astaxanthin oleoresin complex in accordance with a non-limiting example.
Figure 3:
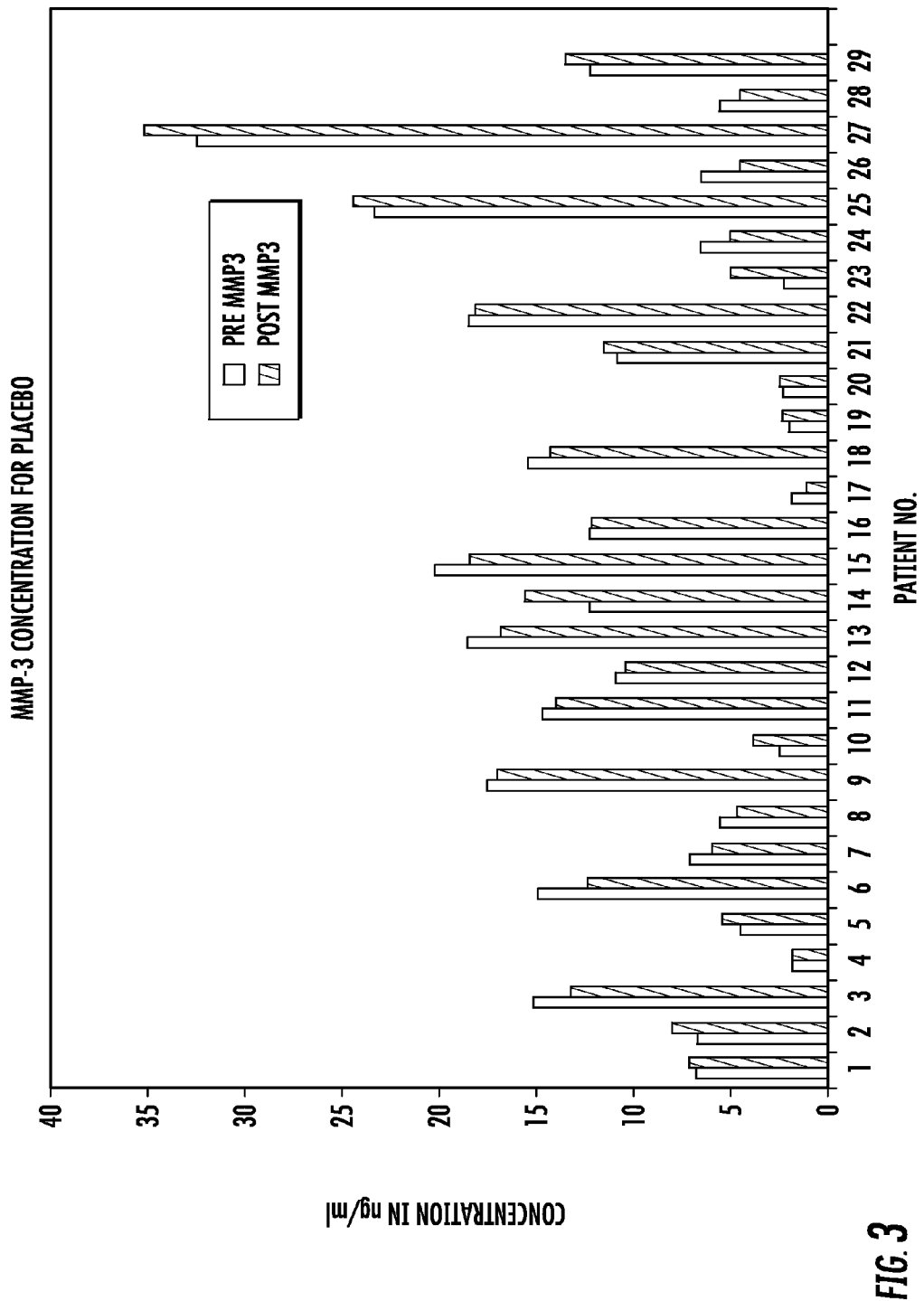
FIG. 3 shows MMP3 results on OA patients administered with placebo.

Assessment of Osteoarthritis symptoms based on haematological studies, specifically MMP3 (Matrix metalloproteinase 3) were carried out in clinical parameters since Osteoarthritis patients show elevated levels of MMP3 in blood as well as in synovial fluid. The elevated levels cause significant tissue damage through cartilage destruction. The results of the MMP3 analysis on Osteoarthritis patients before and after 3 months of administering with astaxanthin oleoresin complex are given in FIG. 2. The results of the MMP3 analysis on Osteoarthritis patients before and after 3 months of administering with Placebo are given in FIG. 3. MMP3 levels did not show significant change but the trend is towards reduction.

In all, 70 subjects were recruited for the study in a randomized manner. The patients were explained the nature of the study as well as active (astaxanthin oleoresin complex softgels containing 15 mg astaxanthin) and placebo treatments. An informed written consent was obtained from the subjects prior to the commencement of the study. At the commencement of the study patient subjects were clinically examined and blood samples were collected for CBC/ESR & MMP3 study. Specific orthopedic and radiological examinations were performed. The patient subjects were assigned placebo and active treatment in a random manner for a period of 12 weeks. Patient subjects were advised to continue with their other routine treatments, if any. At the end of 4 weeks the subjects were called for a second visit in order to refill the samples. The same procedure was carried out in third visit and the procedure of the first visit was repeated in fourth visit. Results were tabulated by data entry operators and detailed statistical analysis was performed using those results. At the base level the groups were similar and comparable.

Advantages of the Invention

Total Health Assessment score (Arising, Dressing, Eating, Walking, Hygiene, Grip, Reaching, Daily activities) exhibited significant changes between Astaxanthin oleoresin complex and Placebo group (P<0.001). Improvement was seen in all the parameters of daily activities.

WOMAC INDEX exhibited significant differences (P<0.001). This score is unique for the functional abilities in patients with chronic joint disorders such as Osteoarthritis.

VAS Pain parameters (Pain+Physical) score: There were significant reductions in the mean scores at the end of treatment for patients taking astaxanthin oleoresin complex but not for Placebo P (<0.001). It is suggestive of improvement in the pain related aspects of Osteoarthritis.

Laquesne's index: (Functional Index for OA of knee): There were significant reductions in the mean scores at the end of treatment for patients taking Astaxanthin oleoresin complex but not for Placebo (P<0.05).

Sleep scale from the medical outcomes study: There were significant reductions in the mean scores at the end of treatment for patients taking astaxanthin oleoresin complex but not for Placebo (P<0.001).

There was significant difference between the average sleep each night (hrs). Patients taking astaxanthin oleoresin complex had higher sleep than Placebo group (P<0.01).

Improvement in the sleep time clearly indicates efficacy of the treatment with astaxanthin oleoresin complex. Astaxanthin helps to get better sleep as is evident from sleep score. This is due to reduction in pain and other symptoms of the disorder MMP3 did not show significant change but the trend is towards reduction. Reduction in MMP3 levels are suggestive of improving cartilage health due to reduction in the process of cartilage destruction in a positive manner although there is neither direct proof to this effect nor statistically significant effect in the present study. No change in the radiological picture was seen. No noteworthy side effect/intolerance was noted during the study period. Astaxanthin oleoresin complex appears to be safe for general consumption.

Astaxanthin oleoresin complex extracted through polar solvents from *Haematococcus pluvialis* alga may be suitable for the patients in the early stage of the Osteoarthritis to prevent the progression of the disorder. It may be useful to the patients with established Osteoarthritis to provide symptomatic relief from pain and improved quality of life. Astaxanthin oleoresin complex improves symptoms like pain as well as quality of physical activities of daily life in a significant manner. Osteoarthritis is seen to mark its presence at a younger age in India. It would be appropriate to initiate the treatment with Astaxanthin oleoresin complex right from the beginning as soon as the diagnosis is arrived at. Study with larger sample size at different centres is recommended to study the mechanism of action of Astaxanthin oleoresin complex in Osteoarthritis further.

TABLE 1

Carotenoid Profile of *Haematococcus Pluvialis* Cell Powder and Astaxanthin Oleoresin Complex

| Carotenoids | Cell powder | Astaxanthin Oleoresin complex 5% |
| --- | --- | --- |
| Beta-carotene | 0.62 ± 0.01 | 0.62 ± 0.01 |
| Canthaxanthin | 1.21 ± 0.03 | 1.20 ± 0.03 |
| Astacene | 3.09 ± 0.06 | 3.09 ± 0.06 |
| Semiastacene | 1.35 ± 0.03 | 1.35 ± 0.03 |
| Dicis astaxanthin | 1.07 ± 0.02 | 1.03 ± 0.05 |
| Trans astaxanthin | 75.70 ± 1.53 | 75.75 ± 1.51 |
| 9 cis astaxanthin | 9.20 ± 0.77 | 9.19 ± 0.77 |
| 13 cis astaxanthin | 6.10 ± 0.94 | 6.08 ± 0.93 |
| Lutein | 1.66 ± 0.03 | 1.65 ± 0.03 |

TABLE 2

Proximate Analysis, Carotenoid Profile and Fatty Acid Profile of Astaxanthin Oleoresin Complex

| PARAMETER | Astaxanthin oleoresin complex 5% |
| --- | --- |
| PHYSICAL | |
| Appearance | Free flow |
| Color | Dark red |
| PROXIMATE | |
| Protein % | 0.95 ± 0.03 |
| Carbohydrate % | 0.11 ± 0.01 |
| Lipid % | 94.89 ± 0.12 |

TABLE 2-continued

Proximate Analysis, Carotenoid Profile and
Fatty Acid Profile of Astaxanthin Oleoresin Complex

| PARAMETER | Astaxanthin oleoresin complex 5% |
|---|---|
| Ash % | 3.82 ± 0.08 |
| Moisture % | 0.23 ± 0.02 |
| Carotenoids | 5.14 ± 0.04 |
| CAROTENOIDS % | |
| Total carotenoids | 5 |
| Total astaxanthin | 4.68 |
| [all-trans-astaxanthin | [3.90 |
| 9-cis-astaxanthin | 0.47 |
| 13-cis-astaxanthin | 0.31 |
| 15-cis-astaxanthin | 0 |
| Dicis-astaxanthin] | 0.05] |
| Betacarotene | 0.03 |
| Canthaxanthin | 0.06 |
| Lutein | 0.08 |
| FATTY ACID PROFILE, Area % | |
| C 14:0 Myristic acid | 0.23 |
| C 15:0 Pentadecanoic acid | 0.1 |
| C 16:0 Palmitic acid | 24.57 |
| C 16:1 Palmitoleic acid | 0.57 |
| C 16:2 Hexadeca dienoic acid | 0.45 |
| C 16:3 Hexadecatrienoic acid | 0.14 |
| C 16:4 Hexadecatetraenoic acid | 1.15 |
| C 17:0 Heptadecanoic acid | 2.14 |
| C 18:0 Stearic acid | 1.61 |
| C18:1 Oleic acid | 38.93 |
| C 18:2 Linoleic acid | 17.22 |
| C 18:3, n-6 Gamma linolenic acid | 0.84 |
| C 18:3, n-3 Alpha linolenic acid | 8.14 |
| C 18:4 Octadeca tetraenoic acid | 1.3 |
| C 20:2 Eicosadienoic acid | 0.81 |
| C 20:4 Arachidonic acid | 0.85 |
| C 22:0 Behenic acid | 0.5 |

TABLE 3

Total Health Assessment Score
Total Health Assessment Score

| | | Duration | | | Significance |
|---|---|---|---|---|---|
| Treatments | Basal | 1 month | 2 months | 3 months | level |
| Astaxanthin | 18 | 14.68 | 13.19 | 12.13 | S, P < 0.001 |
| Placebo | 20.25 | 19.8 | 19.48 | 19.51 | NS, P = 0.4 |

S = Significant,
NS = Not Significant,
P = Probability

TABLE 4

WOMAC Score
WOMAC

| | | Duration | | | Significance |
|---|---|---|---|---|---|
| Treatments | Basal | 1 month | 2 months | 3 months | level |
| Astaxanthi | 36.3 | 31.87 | 28.42 | 26.52 | S, P < 0.001 |
| Placebo | 38.07 | 36.62 | 36.59 | 36.1 | NS, P = 0.6 |

S = Significant,
NS = Not Significant,
P = Probability

TABLE 5

VAS Pain Parameters Score
Pain Parameters

| | | Duration | | | Significance |
|---|---|---|---|---|---|
| Treatments | Basal | 1 month | 2 months | 3 months | level |
| Astaxanthi | 891.94 | 828.71 | 772.58 | 748.39 | S, P < 0.001 |
| Placebo | 945.86 | 923.28 | 916.21 | 915.17 | NS, P = 0.1 |

S = Significant,
NS = Not Significant,
P = Probability

TABLE 6

Laquesne's Index

| Parameters | | Astaxanthin | Placebo | Significance level |
|---|---|---|---|---|
| 1. During nocturnal bed rest | Basal | 0.6 +/− 0.7 | 0.6 +/− 0.7 | NS, P = 1.0 |
| | 3 months | 0.8 +/− 0.7 | 0.5 +/− 0.7 | S, P = 0.05 |
| 2. Morning stiffness or Regressive pain after rising | Basal | 0.9 +/− 0.6 | 0.6 +/− 0.7 | NS, P = 0.9 |
| | 3 months | 0.6 +/− 0.6 | 0.6 +/− 0.5 | NS, P = 0.9 |
| 3. After standing for 30 Minutes | Basal | 0.4 +/− 0.5 | 0.6 +/− 0.7 | NS, P = 0.9 |
| | 3 months | 0.3 +/− 0.6 | 0.5 +/− 0.7 | S, P = 0.05 |
| 4. Maximum distance walked | Basal | 1.3 +/− 0.7 | 1.7 +/− 1.3 | NS, P = 0.9 |
| | 3 months | 0.6 +/− 0.5 | 1.7 +/− 1.3 | S, P = 0.001 |
| 5. Activities of daily living | | | | |
| a) Able to climb up a standard flight of stairs | Basal | 0.8 +/− 0.5 | 0.9 +/− 0.3 | NS, P = 0.9 |
| | 3 months | 0.7 +/− 0.5 | 1.0 +/− 0.4 | S, P = 0.03 |
| b) Able to climb down a standard flight of stairs | Basal | 1.3 +/− 0.3 | 1.6 +/− 0.9 | NS, P = 0.9 |
| | 3 months | 0.9 +/− 0.6 | 1.6 +/− 0.9 | S, P = 0.03 |
| c) Able to squat or bend the Knees | Basal | 1.3 +/− 0.3 | 1.6 +/− 0.9 | NS, P = 0.9 |
| | 3 months | 0.9 +/− 0.6 | 1.6 +/− 0.9 | S, P = 0.03 |
| d) Able to walk on uneven Ground | Basal | 1.3 +/− 0.3 | 1.6 +/− 0.9 | NS, P = 0.9 |
| | 3 months | 0.9 +/− 0.6 | 1.6 +/− 0.9 | S, P = 0.03 |

S = Significant,
NS = Not Significant,
P = Probability

TABLE 7

Sleep Scale MOS

| Sleep parameters | | Astaxanthin | Placebo | Significance level |
|---|---|---|---|---|
| 1. Time to fall asleep (min) during the past 4 weeks | Basal | 2.3 +/− 1.3 | 2.6 +/− 1.3 | NS, P = 0.9 |
| | 3 months | 1.6 +/− 1.1 | 2.5 +/− 1.3 | S, P < 0.001 |
| 2. Average sleep each night (hours during last 4 weeks) | | 6. +/− 1.3 | 5. +/− 1.8 | S, P < 0.001 |
| 3. Feel your sleep was not quiet? | Basal | 3. +/− 1.9 | 3. +/− 1.8 | NS, P = 0.9 |
| | 3 months | 2.6 +/− 2.1 | 3.8 +/− 2.1 | S, P = 0.02 |
| 4. Get enough sleep to feel rested upon? | Basal | 3.8 +/− 1.9 | 3.8 +/− 1.9 | NS, P = 1. 0. |
| | 3 months | 2.9 +/− 2.1 | 3.6 +/− 2.1 | S, P = 0.03 |
| 5. Awaken short of breath or with headache? | Basal | 5.6 +/− 1.2 | 4.6 +/− 2.2 | NS, P = 0.6 |
| | 3 months | 5.6 +/− 1.2 | 4.5 +/− 2.8 | NS, P = 0.6 |
| 6. Feel drowsy or sleepy during day? | Basal | 5. +/− 1.2 | 4. +/− 2.2 | NS, P = 0.6 |
| | 3 months | 5.7 +/− 1.8 | 4.5 +/− 2.8 | NS, P = 0.6 |
| 7. Have trouble falling asleep? | Basal | 3.6 +/− 2.7 | 4.6 +/− 2.2 | NS, P = 0.3 |
| | 3 months | 4.4 +/− 2.1 | 4.5 +/− 2.8 | NS, P = 0.9 |
| 8. Awaken during your sleep time and have trouble in falling sleep again? | Basal | 4.1 +/− 2.9 | 4.6 +/− 2.2 | NS, P = 0.7 |
| | 3 months | 4.9 +/− 2.3 | 4.5 +/− 2.8 | NS, P = 0.7 |
| 9. Have trouble staying awake during the day? | Basal | 4.7 +/− 1.8 | 4.6 +/− 2.2 | NS, P = 0.9 |
| | 3 months | 5.4 +/− 1.8 | 4.5 +/− 2.8 | S, P = 0.05 |
| 10. Snore during your sleep? | Basal | 5.5 +/− 1.1 | 4.4 +/− 1.5 | NS, P = 0.2 |
| | 3 months | 5.7 +/− 0.8 | 4.8 +/− 1.3 | S, P = 0.05 |
| 11. Take naps (5 min. or longer) during the day? | Basal | 4.1 +/− 1.5 | 4.4 +/− 1.5 | NS, P = 0.6 |
| | 3 months | 3.7 +/− 1.5 | 4.8 +/− 1.3 | S, p = 0.05 |
| 12. Get the amount of sleep you needed? | Basal | 3.2 +/− 1.8 | 4.5 +/− 1.5 | NS, P = 0.6 |
| | 3 months | 3.7 +/− 1.8 | 4.8 +/− 1.3 | S, P = 0.05 |

S = Significant,
NS = Not Significant,
P = Probability

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method to treat and alleviate symptoms of joint pain in a patient by administering a therapeutic amount of a dietary supplement composition including a krill oil in combination with astaxanthin and low molecular weight of hyaluronic acid or sodium hyaluronate (hyaluronan) having a molecular weight of between 0.5 and 100 kilodaltons (kDa) in an oral dosage form.

2. The method according to claim 1, wherein the krill oil is derived from *Euphasia* spp., comprising Eicosapentaenoic (EPA) and Docosahexaenoic (DHA) fatty acids in the form of triacylglycerides and phospholipids.

3. The method according to claim 2, wherein the krill oil includes at least 10% EPA and 5% DHA, of which not less than 40% are in the form of phospholipids.

4. The method according to claim 1, and further comprising delivering 1-4000 mg of krill oil per daily dose.

5. The method according to claim 1 and further comprising delivering 0.1-50 mg astaxanthin supplemented to the krill oil per daily dose.

6. The method according to claim 1, wherein the astaxanthin is derived from *Haematococcus pluvialis* algae, *Pfaffia*, krill, or by synthetic routes, in the free diol, monoester or diester form.

7. The method according to claim 1, wherein the low molecular weight hyaluronic acid or sodium hyaluronate (hyaluronan) are derived from microbial fermentation or animal tissue.

8. The method according to claim 7, and further comprising delivering 1-500 mg of hyaluronan per daily dose.

9. The method according to claim 8, wherein the hyaluronan is micro- or nano-dispersed within the composition.

10. The method according to claim 7, wherein the hyaluronic acid is derived from a biofermentation process.

11. The method according to claim 1, wherein the composition further includes a natural or synthetic cyclooxygenase-1 or -2 inhibitor comprising aspirin, acetaminophen, steroids, prednisone, or NSAIDs.

12. The method according to claim 1, wherein the composition further includes a gamma-linoleic acid rich oil comprising Borage (*Borago officinalis* L.) or Safflower (*Carthamus tinctorius* L.).

13. The method according to claim 1, wherein the composition further includes an n-3 (omega-3) fatty acid rich oil derived from fish oil, algae oil, flax seed oil, perrila seed oil or chia seed oil and the n-3 fatty acid comprises alpha-linolenic, stearidonic, eicosapentaenoic or docosapentaenoic acid.

14. The method according to claim 1, wherein the composition further includes at least one of collagen and elastin.

15. The method according to claim 1, wherein the composition further includes anti-inflammatory and/or joint health promoting compounds comprising at least one of preparations of green lipped mussel (*Perna canaliculus*), *Boswellia serrata*, turmeric (*Curcuma longa*), stinging nettle (*Urtica dioica*), Andrographis, Cat's claw (*Uncaria tomentosa*), bromelain, methylsulfonylmethane (MSM), chondroitin sulfate, glucosamine sulfate, s-adenosyl-methionine, proanthocyanidins, procyanidins or flavonoids, and preparations of hydrolyzed or un-hydrolyzed eggshell membrane.

16. The method according to claim 1, wherein the composition further includes naturally-derived and synthetic antioxidants that are added to retard degradation of polyunsaturated fatty acids and astaxanthin.

17. A method to treat and alleviate symptoms of non-disease state joint pain in a patient by administering a therapeutic amount of a dietary supplement composition including a krill oil derived from *Euphasia* spp., comprising Eicosapentaenoic (EPA) and Docosahexaenoic (DHA) fatty acids in the form of triacylglycerides and phospholipids and includes at least 10% EPA and 5% DHA, of which not less than 40% are in the form of phospholipids, and in combination with astaxanthin and low molecular weight hyaluronic acid or sodium hyaluronate (hyaluronan) having a molecular weight of between 0.5 and 100 kilodaltons (kDa) in an oral dosage form.

18. The method according to claim 17, and further comprising delivering 1-4000 mg of krill oil per daily dose.

19. The method according to claim 17, and further comprising delivering 0.1-50 mg astaxanthin supplemented to the krill oil per daily dose.

20. The method according to claim 17, wherein the astaxanthin is derived from *Haematococcus pluvialis* algae, *Pfaffia*, krill, or by synthetic routes, in the free diol, monoester or diester form.

21. The method according to claim 17, wherein the low molecular weight hyaluronic acid or sodium hyaluronate (hyaluronan) are derived from microbial fermentation or animal tissue.

22. The method according to claim 21, and further comprising delivering 1-500 mg of hyaluronan per daily dose.

23. The method according to claim 22, wherein the hyaluronan is micro- or nano-dispersed within the composition.

\* \* \* \* \*

UNITED STATES PATENT AND TRADEMARK OFFICE
CERTIFICATE OF CORRECTION

PATENT NO. : 8,481,072 B2
APPLICATION NO. : 12/840372
DATED : July 9, 2013
INVENTOR(S) : Minatelli et al.

Page 1 of 1

It is certified that error appears in the above-identified patent and that said Letters Patent is hereby corrected as shown below:

In the Claims:

Claim 1: Column 19, Line 44

Delete:
 "low molecular weight of hyaluronic acid"

Insert:
 -- low molecular weight hyaluronic acid --

Signed and Sealed this
Third Day of September, 2013

Teresa Stanek Rea
*Acting Director of the United States Patent and Trademark Office*